(12) United States Patent
Buisine et al.

(10) Patent No.: US 7,902,409 B2
(45) Date of Patent: Mar. 8, 2011

(54) PRODUCTION OF DIFLUOROETHANOL

(75) Inventors: Olivier Buisine, Saint Genis Laval (FR); Roland Jacquot, Francheville (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 12/086,747

(22) PCT Filed: Dec. 19, 2006

(86) PCT No.: PCT/FR2006/002780
§ 371 (c)(1),
(2), (4) Date: Feb. 19, 2009

(87) PCT Pub. No.: WO2007/071841
PCT Pub. Date: Jun. 28, 2007

(65) Prior Publication Data
US 2009/0221859 A1    Sep. 3, 2009

(30) Foreign Application Priority Data

Dec. 19, 2005  (FR) .................................... 05 12902

(51) Int. Cl.
*C07C 31/38*    (2006.01)
(52) U.S. Cl. ......................................... 568/842; 568/861
(58) Field of Classification Search ................. 568/842, 568/861
See application file for complete search history.

(56) References Cited

FOREIGN PATENT DOCUMENTS

EP    1224971 A1    7/2002
JP    61268639      4/1987

OTHER PUBLICATIONS

Henne et al., "Acidity of Trifluorinated Alcohols and Saponification Rates of their Acetates", Journal of the American Chemical Society, Mar. 1962, pp. 1426-1428. vol. 74.
International Search Report corresponding to PCT/FR 2006/002780.

*Primary Examiner* — Sikarl A Witherspoon
(74) *Attorney, Agent, or Firm* — Buchanan Ingersoll & Rooney PC

(57) ABSTRACT

Difluoroethanol is produced by hydrogenation, in the presence of an effective amount of a catalyst containing at least one element of Group VIII of the Periodic Table deposited onto a solid, acidic mineral support, of an acetyl halide having the following formula (I), in which formula X is a halogen atom other than a fluorine atom:

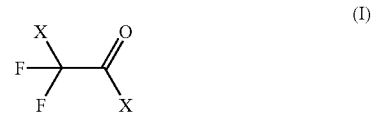

27 Claims, No Drawings

PRODUCTION OF DIFLUOROETHANOL

CROSS-REFERENCE TO PRIORITY/PCT APPLICATIONS

This application claims priority under 35 U.S.C. §119 of FR 0512902, filed Dec. 19, 2005, and is the national phase of PCT/FR 2006/002780, filed Dec. 19, 2006 and designating the United States (published in the French language on Jun. 28, 2007, as WO 2007/071841 A2; the title and abstract were also published in English), each hereby expressly incorporated by reference in its entirety and each assigned to the assignee hereof.

A subject matter of the present invention is a novel process for the preparation of difluoroethanol.

Difluoroethanol is an alcohol used in organic synthesis, in particular in the field of agrochemistry and of pharmaceuticals.

Various process for the synthesis of difluoroethanol have already been proposed.

It is possible in particular to produce difluoroethanol by reduction of difluoroacetyl chloride, either with hydrides [A. L. Henne and R. L. Pelley, JACS, 74 (1952), 1426-8] or by catalytic hydrogenation [Asahi Chemical, Patent JP61268639 of May 24, 1985], or by reduction of ethyl difluoroacetate using sodium borohydride [M. Lewis and E. de Clerck, J Chem. Res., Miniprint 8 (2001), 844-56].

Mention may also be made of the reduction of difluoroacetic acid by the borane/dimethyl sulfide complex [W. G. Reifenrath and E. B. Roche, J Med. Chem., 23 (9), (1980), 985-90].

However, these processes require several stages of synthesis starting from difluoroacetic acid or employ expensive reactants which render them processes which are complex and not economically viable.

Another access route to difluoroethanol consists in carrying out the hydrolysis of 2,2-difluoro-1-bromoethane between 150 and 200° C. The yields reported are approximately 50%.

The object of the present invention is to provide a process for the preparation of difluoroethanol starting from a readily accessible reactant.

There has now been found, and it is this which constitutes the subject matter of the present invention, a process for the preparation of difluoroethanol, characterized in that it comprises a hydrogenation, in the presence of an effective amount of a catalyst comprising at least one element from Group VIII of the Periodic Table deposited on a solid inorganic support having acid properties, of an acetyl halide corresponding to the following formula:

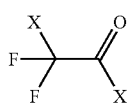
(I)

in said formula, X represents a halogen atom other than a fluorine atom.

In the formula (I), X represents a chlorine, bromine or iodine atom.

The process of the invention applies very particularly to a substrate corresponding to the formula (I) in which X represents a chlorine atom.

In accordance with the process of the invention, a triple catalytic hydrogenation is carried out, namely the reduction of the carbonyl group and a double dehydrohalogenation.

Use is made, as preferred hydrogenation catalyst, of a metal element chosen from the elements from Group VIII of the Periodic Table of the Elements.

For the definition of the elements, reference is made below to the Periodic Table of the Elements published in the Bulletin de la Société Chimique de France, No. 1 (1966).

They are more particularly noble metals, such as: ruthenium, rhodium, palladium, osmium, iridium or platinum.

Use may also be made of a mixture of said elements.

Mention may be made, as metal elements preferably employed, of palladium and/or platinum.

The metal can be deposited on the support in the form of a finely divided metal or in the form of a compound which will be reduced to the metal in the presence of hydrogen. Thus, it can be employed in the form of an inorganic derivative, such as an oxide or a hydroxide. It is possible to resort to an inorganic salt, preferably nitrate, sulfate, oxysulfate, halide, oxyhalide, silicate or carbonate, or to an organic derivative, preferably cyanide, oxalate, acetylacetonate, alkoxide, more preferably still methoxide or ethoxide, or carboxylate, more preferably still acetate. Complexes, in particular chlorinated complexes, of said noble metal and/or of alkali metals, preferably sodium or potassium, or of ammonium can also be employed.

The choice of support is conditioned by the fact that it has to be an inorganic solid having Lewis acid properties or which can develop a Lewis acidity in the presence of hydrochloric acid released in the process of the invention.

Reference may be made, for the definition of a Lewis acid, inter alia, to the work by Jerry March, Advanced Organic Chemistry, 8, p. 260 (1992).

The Lewis acid is defined as any chemical entity exhibiting a vacant orbital and consequently capable of accepting electrons.

In the preferred embodiment of the invention, the support comprises alumina and is an inorganic solid which develops a Lewis acid $AlCl_3$.

Recourse may be had, as examples of supports suitable for the process of the invention, to alumina and to compounds comprising it.

Alumina is the support preferably chosen in the process of the invention. It can be α-, γ- or η-alumina. γ-Alumina is preferred.

Mention may be made, as regards the alumina-comprising supports, of any natural or synthetic aluminosilicate and more particularly of acid clays and acid zeolites.

A first type of inorganic support which is entirely well suited to the implementation of the process of the invention is that of acid clays.

Mention may be made, as preferred examples, of montmorillonites. They can be represented by the formula $3SiO_2 \cdot Al_2O_3 \cdot (Mg, Ca)O \cdot nH_2O$, with n between 5 and 7. Mention may also be made of bentonite.

Recourse is preferably had to commercial clays which are already acidic, such as in particular the following clays: Tonsil Optimum FF and K 10.

If necessary, the commercial clays can be treated using an aqueous solution of a strong acid. The treatment is carried out by a person skilled in the art in a conventional fashion. It is possible, for example, to introduce the clay into an aqueous sulfuric acid solution with a pH of between 2 and 4.

Mention may be made, as other supports suitable for the invention, of zeolites.

Natural zeolites are materials belonging to the family of the hydrated aluminosilicates of metals from Groups Ia and IIa of the Periodic Table of the Elements (for example: calcium, magnesium, potassium, and the like).

Structurally, zeolites are crystalline inorganic polymeric complexes based on an infinite three-dimensional succession of structures connected at four points formed of tetrahedral $AlO_4$ and $SiO_4$ bonded to one another via an exchange of oxygen ions. Each tetrahedral $AlO_4$ present in the structure contributes a strong negative charge which is counterbalanced by a cation ($Ca^{2+}$, $Mg^{2+}$, and the like).

Two kinds of zeolites exist: natural zeolites and synthetic zeolites, both of which can be involved in the process of the invention.

Mention may be made, as examples of zeolitic supports suitable for the present invention, of natural zeolites, such as, for example: chabazite, clinoptilolite, erionite, mordenite, phillipsite or offretite.

Synthetic zeolites are preferably suitable for the implementation of the invention. The choice is very particularly made of zeolites such as zeolite HZSM-5 of MFI type, zeolite HZSM-11 of MEL type, zeolite HY of faujasite (FAU) type, H-mordenite (MOR) or zeolite KL.

Zeolites are known products which are widely described in the literature, in particular in "Atlas of zeolites structure types" by W. M. Meier and D. H. Olson, published by the Structure Commission of the International Zeolite Association (1992), p. 132.

It is preferable to employ, in the process of the invention, synthetic zeolites and more particularly the commercial zeolites which are in the following forms:

zeolites HZSM-5 or aluminum silicalite with an Si/Al molar ratio of 10 to 500;
zeolite ZSM-11 with an Si/Al atomic ratio of 5 to 30,
zeolites HY with an Si/Al atomic ratio of 2.3 to 40,
H-mordenite with an Si/Al atomic ratio of 5 to 45.

Recourse is preferably had to the commercial zeolites HY or H-mordenite in the acid form, such as zeolites of HY type, such as CBV 720, with an Si/Al atomic ratio respectively equal to 15, sold by Zeolyst, and zeolites of H-mordenite type, such as CBV 20 A and 90 A, with an Si/Al atomic ratio respectively equal to 10 and 45.

In accordance with the invention, the catalyst comprises a metal element from Group VIII deposited on the supports as defined above.

Deposition on the support is carried out according to techniques commonly used by a person skilled in the art, for example impregnation on the support.

Generally, the metal is deposited in a proportion of 0.1% to 10%, preferably of 0.5% to 5%, of the weight of the catalyst.

Use is preferably made of platinum- and/or palladium-based catalysts deposited on an alumina support.

Preferably, the platinum and/or the palladium is deposited on said support in a proportion of 0.5% to 5% of the weight of the catalyst.

The catalyst can be employed in the form of a powder, pellets or also granules.

In accordance with the process of the invention, a catalytic hydrogenation is carried out on the starting substrate.

The amount of hydrogen employed is at least 2 mol per mole of substrate. It is preferably between 2 and 10 and preferentially between 3 and 10.

The process of the invention can be carried out in the vapor phase or in the liquid phase.

A preferred embodiment of the invention consists in carrying out the process of the invention in the vapor phase.

The temperature is then chosen within a temperature range extending from 150° C. to 350° C. and more particularly between 200° C. and 300° C.

The reaction takes place under a hydrogen pressure ranging from a pressure slightly greater than atmospheric pressure up to a pressure of several bar. Advantageously, the hydrogen pressure varies between 1 and 10 bar and more preferably between 1 and 5 bar.

A preferred embodiment of the invention consists in carrying out the process according to the fixed bed technique.

Preferably, the reaction is carried out continuously, in a tubular reactor equipped with heating means, comprising the solid catalyst positioned as a fixed bed.

The catalytic bed is brought to the reaction temperature chosen within the range defined above, over which the hydrogen stream is passed.

The compound of formula (I) is subsequently conveyed over the catalytic bed.

It can also be introduced in a solvent, as defined below.

In the gas phase, the residence time of the material stream over the catalytic bed is very short and generally varies between less than one second to approximately 1 min: the pressure is also close to atmospheric pressure but it is possible to operate under a pressure which can reach 10 bar.

After passing over the fixed bed, the gas stream is condensed, for example at a temperature of between 20° C. and 40° C.

A liquid phase is obtained which comprises difluoroethanol, which can be recovered conventionally, by distillation or also by liquid/liquid extraction using an immiscible solvent, for example diisopropyl ether.

The uncondensed stream is conveyed to a scrubbing column comprising sodium hydroxide in order to remove the hydrohalic acid formed during the reaction. Thus, the purified hydrogen can be recycled to the reaction.

According to another embodiment of the invention, it is possible to carry out the reaction in the liquid phase.

The temperature of the reaction is then advantageously chosen between 20° C. and 150° C. and preferably between 40° C. and 70° C.

The reaction takes place under a hydrogen pressure ranging from a pressure slightly greater than atmospheric pressure up to a pressure of several tens of bar. Advantageously, the hydrogen pressure varies between 1 and 50 bar and more preferably between 10 and 20 bar.

The reaction can take place in the absence of solvent. However, it is preferable to operate in the presence of a solvent. Use may in particular be made of water or of an inert organic compound, such as an aliphatic or cycloaliphatic and halogenated or nonhalogenated hydrocarbon, preferably hexane, cyclohexane or methylcyclohexane, or a halogenated or nonhalogenated aromatic hydrocarbon, preferably toluene or monochlorobenzene.

According to a batchwise mode, the possible solvent, the compound of formula (I) and the catalyst are charged to the reactor.

The amount of hydrogenation catalyst employed, expressed as weight of catalyst per weight of compound of formula (I), can vary, for example, between 0.5 and 20%, preferably between 0.5 and 5%.

Heating is carried out to the temperature defined above.

The desired hydrogen pressure is applied and is maintained by continuously adding hydrogen.

The reaction medium is kept stirred until consumption of hydrogen has ceased.

It may be wise, while keeping the pressure constant in the reactor, to continuously bleed or to carry out noncontinuous bleeds in order to remove the hydrohalic acid formed during the reaction. Thus, this can be recovered in a scrubbing column comprising sodium hydroxide.

At the end of the reaction, the catalyst is separated according to conventional solid/liquid separating techniques, preferably by filtration.

The product obtained is recovered conventionally, preferably by distillation or by liquid/liquid extraction.

An exemplary embodiment of the invention is given below by way of illustration and without a limiting nature.

In the examples, the degree of conversion corresponds to the ratio of the number of moles of substrate converted to the number of moles of substrate charged and the yield given corresponds to the ratio of the number of moles of product formed to the number of moles of substrate charged.

EXAMPLE 1

20 ml of catalyst composed of 2.5% by weight of palladium supported on beads of alumina of α type are introduced into a tubular nickel reactor with an internal diameter of 2.54 cm which is equipped with a screen which makes it possible to retain the catalyst.

The alumina is of α type and occurs in the form of beads with a diameter of 3 mm.

10 ml of glass powder are introduced above the catalyst in order to vaporize and mix the reactants before passing over the catalyst.

The reactor is then heated to 300° C. using an electric furnace under a stream of 5 l/h of hydrogen.

The system is maintained under these conditions for 30 min and then chlorodifluoroacetyl chloride is injected with a pump at a flow rate of 10 g/h, while maintaining the hydrogen flow rate.

The hydrogenate is then condensed in a receiver immersed in a water bath.

A portion of the hydrochloric acid formed is entrained by the stream of excess hydrogen.

After operating under these conditions for 10 hours, it is found, after quantitatively determining the hydrogenate by gas chromatography, that the conversion of the chlorodifluoroacetyl chloride is 85% and that the difluoroethanol yield is 75%.

EXAMPLE 2

100 g of chlorodifluoroacetyl chloride, 50 g of cyclohexane and 4 g of catalyst comprising 3% by weight of palladium deposited on dry carbon black are introduced into a 300 ml reactor made of Hastelloy B2.

The reactor is purged twice with nitrogen under 10 bar.

Then, with 2 times hydrogen under 10 bar, the reactor is subsequently pressurized under 15 bar, stirred and heated to 75° C.

The pressure is kept constant in the reactor throughout the duration of the reaction.

After 5 hours, hydrogen consumption ceases.

The reactor is purged, the catalyst is filtered off and the reaction medium is analyzed.

All the starting material is converted and the difluoroethanol yield is 60%.

Under these conditions, a mixture of esters composed of difluoroethyl difluoroacetate and difluoroethyl chlorodifluoroacetate is formed.

EXAMPLE 3

Example 1 is reproduced but using, as catalyst, palladium deposited on zeolite HY in a proportion of 3% by weight. In this case, the conversion is 95% and the difluoroethanol yield is 78%.

EXAMPLE 4

Example 1 is reproduced but using, as catalyst, palladium deposited on zeolite HZSM5 in a proportion of 3% by weight. In this case, the degree of conversion is 98% and the difluoroethanol yield is 70%.

EXAMPLE 5

Example 1 is reproduced in an identical fashion but while operating at 350° C.

For a degree of conversion of 100%, a yield of 61% is obtained.

What is claimed is:

1. A process for the preparation of difluoroethanol, comprising hydrogenating, in the presence of an effective amount of a catalyst which comprises at least one element from Group VIII of the Periodic Table deposited onto a solid, acidic inorganic support, an acetyl halide having the following formula:

wherein in said formula (I), X is a halogen atom other than a fluorine atom.

2. The process as defined by claim 1, wherein said acetyl halide has the formula (I) in which X is a chlorine, bromine or iodine atom.

3. The process as defined by claim 1, wherein said catalyst comprises a metal element selected from the group consisting of ruthenium, rhodium, palladium, osmium, iridium and platinum.

4. The process as defined by claim 1, wherein said metal element is deposited onto the support in the form of a finely divided metal or in the form of a compound which will be reduced to the metal in the presence of hydrogen.

5. The process as defined by claim 1, wherein said support comprises alumina or compound thereof.

6. The process as defined by claim 1, wherein said support comprises α-, γ- or η-alumina.

7. The process as defined by claim 1, wherein said support comprises an acid clay.

8. The process as defined by claim 1, wherein said support comprises a natural or synthetic acid zeolite.

9. The process as defined by claim 1, wherein said catalyst is based on palladium and/or platinum deposited onto alumina.

10. The process as defined by claim 1, wherein said hydrogenation is carried out in the vapor phase.

11. The process as defined by claim 1, wherein said hydrogenation is carried out at a temperature ranging from 150° C. to 350° C.

12. The process as defined by claim 1, wherein said hydrogenation is carried out under a hydrogen pressure ranging from 1 to 10 bar.

13. The process as defined by claim 1, wherein the residence time of the reactant over the catalytic bed ranges from less than one second to approximately 1 min.

14. The process as defined by claim 1, wherein said hydrogenation is carried out via a fixed bed reaction.

15. The process as defined by claim 1, wherein said catalyst is heated to the temperature of the reaction, the hydrogen stream is passed therein and then the compound of formula (I) is introduced.

16. The process as defined by claim 1, wherein said hydrogenation is carried out in the liquid phase.

17. The process as defined by claim 1, wherein the hydrogen pressure ranges from 1 to 50 bar.

18. The process as defined by claim 1, wherein said hydrogenation is carried out at a temperature ranging from 20° C. to 150° C.

19. The process as defined by claim 1, wherein said hydrogenation is carried out in an organic solvent selected from among halogenated or non-halogenated aliphatic, cycloaliphatic or aromatic hydrocarbons.

20. The process as defined by claim 1, wherein the amount of hydrogenation catalyst employed, expressed as weight of catalyst per weight of compound of formula (I), ranges from 0.5 to 20%.

21. The process as defined by claim 1, wherein the difluoroethanol is recovered by distillation or by liquid/liquid extraction.

22. The process as defined by claim 2, wherein X is a chlorine atom.

23. The process as defined by claim 3, wherein said metal element comprises palladium and/or platinum.

24. The process as defined by claim 7, wherein said support comprises a montmorillonite.

25. The process as defined by claim 8, wherein said support comprises a zeolite HZSM-5 of MFI type, zeolite HZSM-11 of MEL type, zeolite HY of faujasite (FAU) type, a zeolite H-mordenite or a zeolite KL.

26. The process as defined by claim 17, wherein the hydrogen pressure ranges from 10 to 20 bar.

27. The process as defined by claim 19, wherein said hydrogenation is carried out in hexane, cyclohexane, methylcyclohexane, toluene or monochlorobenzene.

* * * * *